US 6,550,343 B2

(12) United States Patent
Polega

(10) Patent No.: US 6,550,343 B2
(45) Date of Patent: Apr. 22, 2003

(54) METHOD AND APPARATUS FOR TESTING SHEAR STRENGTH OF RUBBER BONDED TO METAL INSERT

(75) Inventor: Dennis M. Polega, Wellsburg, WV (US)

(73) Assignee: Westinghouse Air Brake Technologies Corporation, Wilmerding, PA (US)

( * ) Notice: Subject to any disclaimer, the term of this patent is extended or adjusted under 35 U.S.C. 154(b) by 0 days.

(21) Appl. No.: 09/904,949

(22) Filed: Jul. 13, 2001

(65) Prior Publication Data
US 2003/0010134 A1 Jan. 16, 2003

(51) Int. Cl.[7] .................................................. G01N 3/24
(52) U.S. Cl. ........................................................ 73/842
(58) Field of Search ................................... 73/842, 827

(56) References Cited
U.S. PATENT DOCUMENTS 4,275,600 A * 6/1981 Turner et al. ............... 374/186
4,970,901 A * 11/1990 Takeya et al. ................ 73/827
5,199,301 A * 4/1993 Bauer ........................... 73/168
5,305,637 A * 4/1994 Bauer ........................... 73/168
5,481,903 A * 1/1996 King et al. ................. 73/54.16

* cited by examiner

Primary Examiner—Hezron Williams
Assistant Examiner—Corey D. Mack
(74) Attorney, Agent, or Firm—James Ray & Associates

(57) ABSTRACT

An apparatus for measuring the shear strength of rubber bonded to a metal insert in a valve seal comprising an upper fixture and a lower fixture. A mounting device is disposed in the lower fixture of the apparatus for retaining the valve seal. A shearing means is disposed in the upper fixture of the apparatus for shearing the rubber bonded to the metal insert. The shearing means has an arcuate edge for contacting the valve seal. There is a first means engageable with the shearing means for controlling its movement in one of a downward motion for shearing the valve seal and an upward motion for returning the shearing means to its starting position. Further there is a second means for recording the movement of the shearing means and the force that is applied by such first means until a bond between the rubber and the metal insert of the valve seal is broken.

19 Claims, 4 Drawing Sheets

METHOD AND APPARATUS FOR TESTING SHEAR STRENGTH OF RUBBER BONDED TO METAL INSERT

FIELD OF THE INVENTION

The present invention relates to rubber bonded to metal inserts, and, more particularly, the present invention relates to an apparatus and a method for testing the shear strength of rubber bonded to a metal insert in a valve seal.

BACKGROUND OF THE INVENTION

Check valves are an integral part of countless pieces of equipment in the railroad industry. Valve seals are an integral part of check valves. Valve seals are commonly made of rubber with a metal insert bonded to the rubber. The insert provides the strength while the rubber provides a seal.

It is important to know the shear strength of the rubber that is bonded to the metal insert. If the bond is not strong enough the rubber can be sheared away from the metal during a sealing operation and valve seal cannot perform its function.

Existing technology and all of the ASTM tests that are presently available do not provide an accurate measurement of the shear strength of the rubber bonded to a metal insert in valve seals. One of the major problems is that the existing technology, while excellent for many applications, does not give an accurate reading where the surface area that is being measured is small as it is in valve seals of check valves.

SUMMARY OF THE INVENTION

Therefore, the present invention provides an apparatus for measuring a shear strength of rubber bonded to a metal insert in a valve seal. The apparatus comprises an upper fixture and a radially opposed lower fixture. At least one of the upper fixture and lower fixture being movable in a longitudinal direction with respect to one another.

There is a mounting device disposed in one of the lower fixture and upper fixture of the apparatus for retaining such valve seal. A shearing means is disposed in an opposing one of the upper fixture and the lower fixture of apparatus for shearing such rubber bonded to such metal insert in the valve seal. The shearing means has an arcuate edge for contacting the valve seal closely adjacent an interface between such rubber and such metal insert.

A first means that is engageable with the shearing means controls movement of the shearing means in one of a direction for shearing the valve seal and an opposite direction for returning the shearing means to its starting position. There is further a second means that is in communication with the first means for recording such movement of the shearing means and for recording the force that is applied by the first means until such bond between such rubber and such metal insert of the valve seal is broken.

Another embodiment of the invention provides a method for testing the shear strength of rubber bonded to a metallic insert. The method comprises a first step of selecting a valve seal to be tested, followed by mounting the valve seal, that was selected in the previous step, in one of an upper and a lower fixture of a test apparatus.

A shearing means, disposed in an opposite one of the upper fixture and lower fixture of said test apparatus, is moved in a shearing direction by applying a force to the opposite one of the upper fixture and the lower fixture. Such movement is continued in the shearing direction of the opposite one of the upper fixture and the lower fixture of said test apparatus until a bond between such rubber and such metallic insert is broken.

There is a step in which the total movement of the opposite one of the upper fixture and the lower fixture of the test apparatus is measured, in a predetermined unit of distance. Such measurement further includes measuring, in a predetermined unit of force, the total force applied to the opposite one of upper fixture and lower fixture of test apparatus that is required to break such bond between such rubber and such metallic insert.

There is a step of recording such total movement of the opposite one of the upper fixture and the lower fixture of the test apparatus and such total force applied to the opposite one of the upper fixture and the lower fixture of said test apparatus that was measured in a previous step. Such movement and such force is plotted on a graph.

OBJECTS OF THE INVENTION

It is one of the primary objects of the present invention to provide an apparatus for testing the shear strength of rubber bonded to a metal insert in a valve seal.

It is also an object of the present invention to provide an apparatus which can perform a reliable test on a small surface area.

Another object of the present invention is to provide an apparatus which will provide a printed record of force required to break the bond between the rubber and the metal.

It is yet another object of the present invention to provide a method for testing the shear strength of rubber bonded to a metal insert.

In addition to the numerous objects and advantages of the present invention which have been described with some degree of particularity above, it should be both noted and understood that a number of other important objects and advantages of the lighting system will become more readily apparent to those persons who are skilled in the relevant art from the following more detailed description of the invention, particularly, when such detailed description is taken in conjunction with the appended claims.

Figure 1:
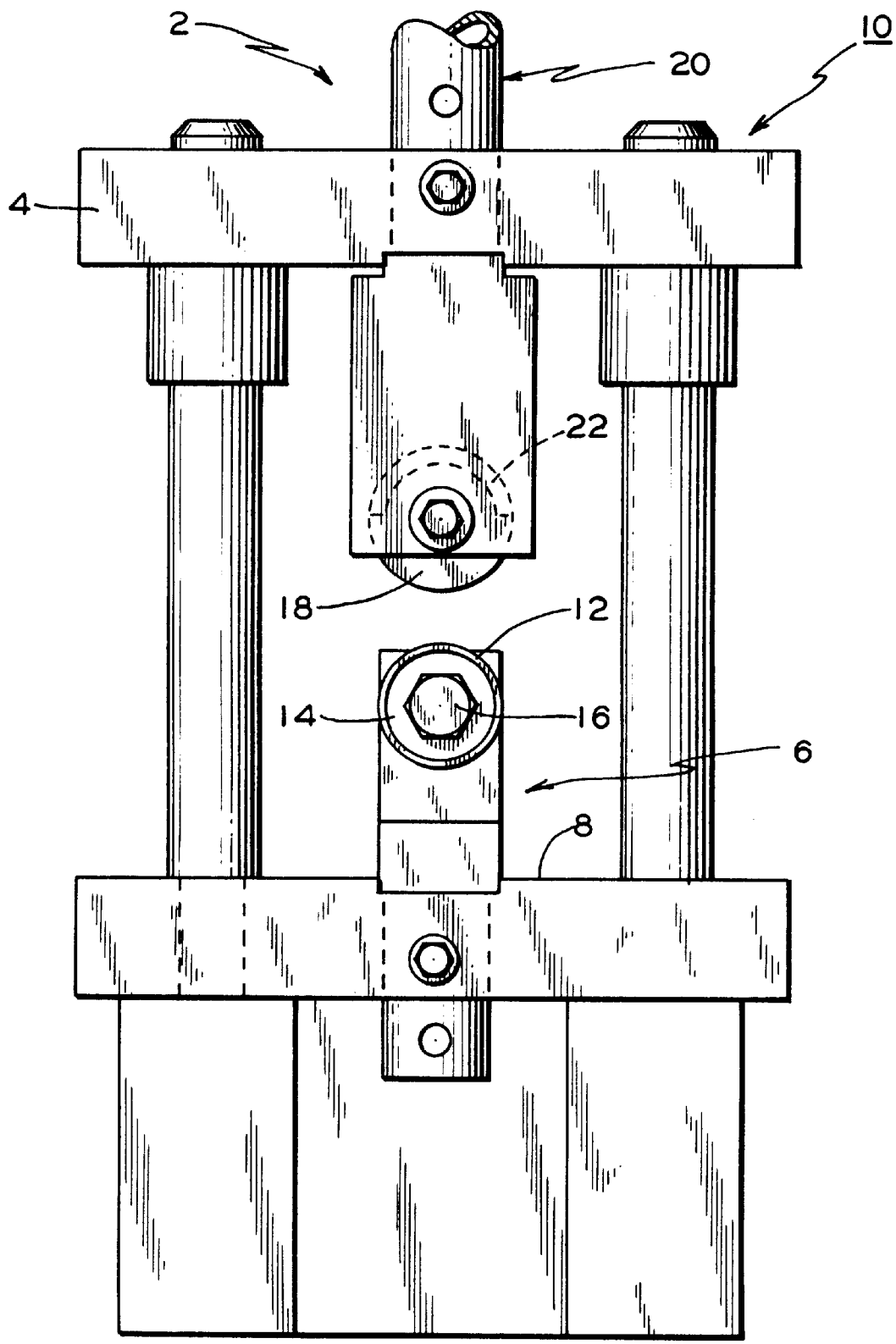
FIG. 1 is a partial perspective frontal view of the apparatus for testing the shear strength of rubber bonded to a metal insert.
Figure 2:
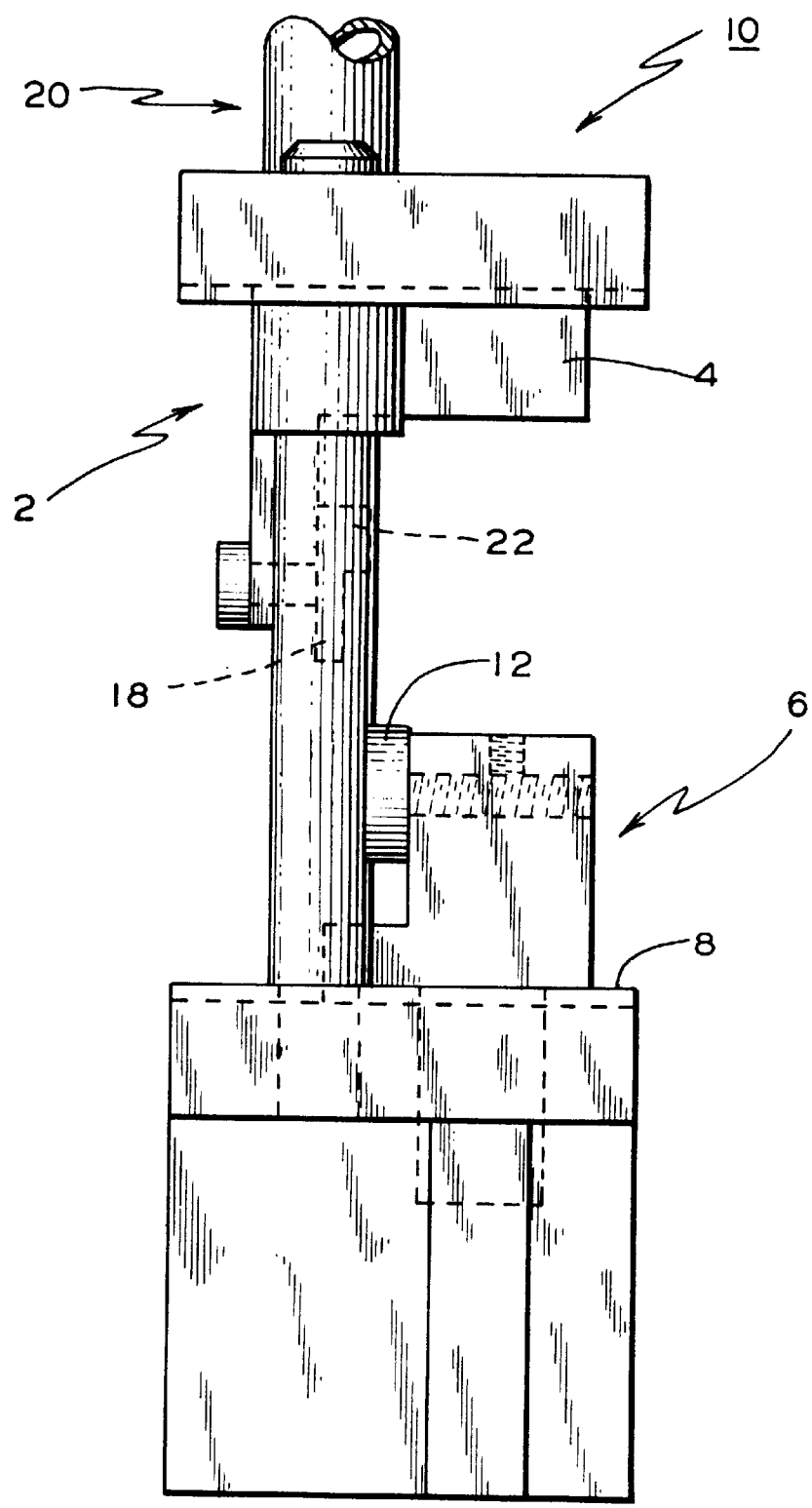
FIG. 2 is a partial perspective side view of the apparatus for testing the shear strength of rubber bonded to a metal insert.

BRIEF DESCRIPTION OF THE PRESENTLY PREFERRED AND VARIOUS ALTERNATE EMBODIMENTS OF THE PRESENT INVENTION

Prior to proceeding to the more detailed description of the present invention, it should be noted that for the sake of clarity in understanding the invention, identical components with identical functions have been designated with identical reference numerals throughout the drawing Figures.

The present invention, illustrated in FIGS. 1 to 5, provides an apparatus, generally designated 10, for testing a bonded rubber to metal insert having a relatively small surface area. The apparatus 10 comprises an upper fixture, generally designated 2, which includes an upper mount 4. There is a radially opposed lower fixture, generally designated 6, which includes a lower mount 8. The description that follows will describe the apparatus in which the upper fixture is a movable fixture which moves in a downward direction as a shearing direction and the lower fixture as being stationary. This is presently preferred embodiment. However, it is within the realm of the invention that the upper fixture could be a stationary fixture while the lower fixture being the movable one and the shearing direction being an upward direction.

A mounting device 12 is disposed in lower fixture 6 for retaining the valve seal 14 that is being tested. The mounting device 12 is designed to simulate the part in its actual state as mounted in the hardware. The valve seal 14 is mounted in mounting device 12 of lower fixture 6 and is held in place with a retainer bolt 16. This also simulates mating hardware in an actual operation. Such retainer bolt 12 has a new improved design which has a thinner head permitting such retainer bolt 12 to hold the valve seal 14 in place while not interfering with the shearing operation.

A shearing means 18 is disposed in upper fixture 2 for shearing such rubber bonded to such metal insert in said valve seal 14. The shearing means 18 has an arcuate edge 22 for contacting the valve seal 14 closely adjacent an interface between such rubber and such metal insert in the valve seal 14. The arcuate edge 22 is not sharp. The edges are radii to promote an actual side force as the part encounters the valve seal 14 in the application.

Figure 5:
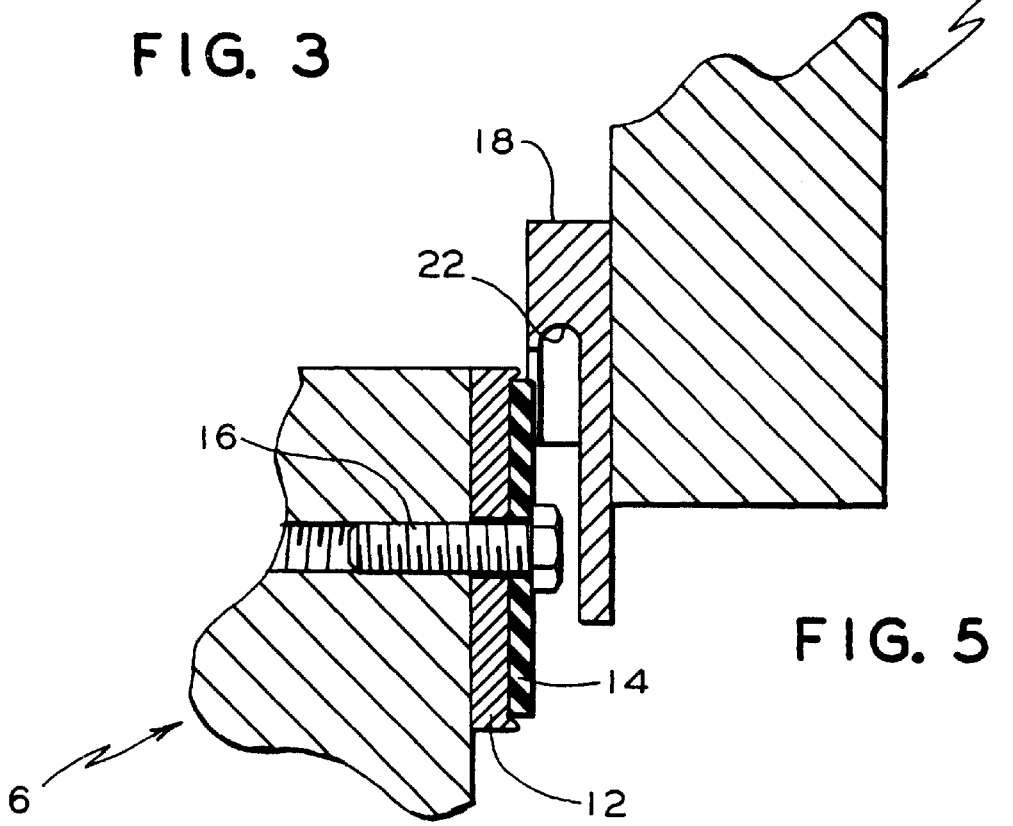
FIG. 5 is a partial perspective side view of the shearing means and the valve seal being tested.

The shearing means 18 of upper fixture 2 and the mounting device 12 of lower fixture 6 are designed so that the point of shear on the rubber part of the valve seal 14 is less than 0.005 inches from the outer surface of the brass insert. It is designed in this manner so that the apparatus will test the bond strength of the rubber to metal insert rather than the tear strength of the rubber itself. FIG. 5 shows an enlarged view of the valve seal 14 mounted in such mounting device 14 of lower fixture 6 and such searing means 18 in a position to shear the valve seal 14.

The apparatus 10 includes a first means, generally designated 20, that is engageable with such shearing means 18 for controlling movement of the shearing means 18, disposed on upper fixture 2, in one of a direction for shearing the valve seal 14 and an opposite direction for returning the shearing means 18 to its starting position. Such first means 20 includes a load cell 24 and a computer module 42 which controls the application of force and such movement of the upper fixture 2.

There is further a second means, generally designated 30, that is in communication with the first means 20 for recording such movement of the shearing means 18 and for recording a force that is applied by the first means 20 until such bond between such rubber and such metal insert of the valve seal 14 is broken.

The second means 30 records the force in pounds and the movement of upper fixture 2 in inches until the bond is broken. The record is in the form of a graph and the graph is printed and filed as a record of the shear strength of such test specimen.

Figure 4:
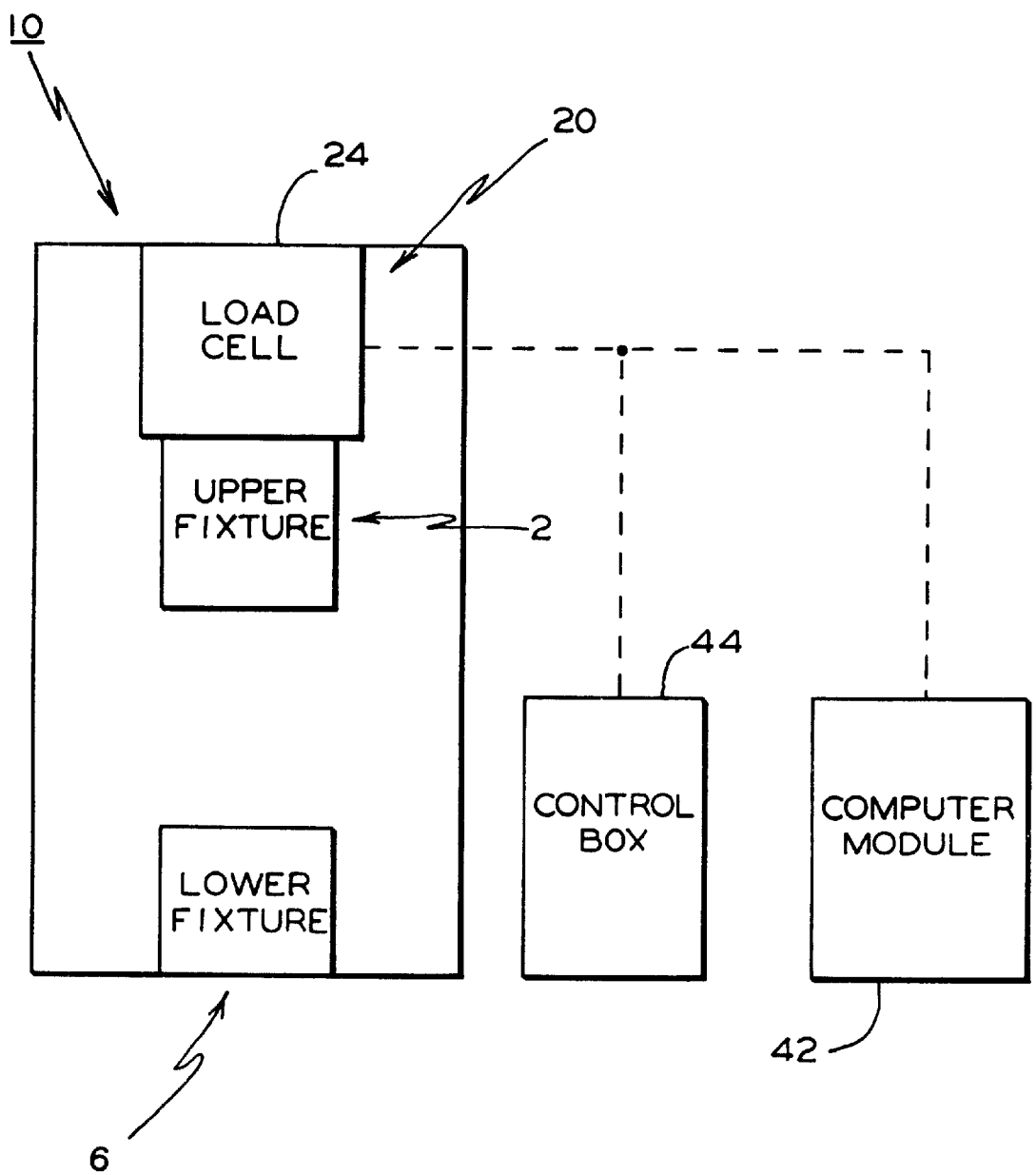
FIG. 4 is a block diagram of the apparatus for testing the shear strength of rubber bonded to a metal insert and ancillary modules.

It is also an embodiment of the invention for such apparatus to further include a third means, generally designated 40, that is in communication with the second means 20 for displaying such distance the shearing means 18 has moved and such force that was applied to the shearing means 18. It is presently preferred that such first means 20, such second means 30, and such third means 40 are all incorporated in the software programmed into the computer module. Such display of the graph can be seen on the monitor of the computer 42. FIG. 4 is a block diagram showing the apparatus with the ancillary modules.

Figure 3:
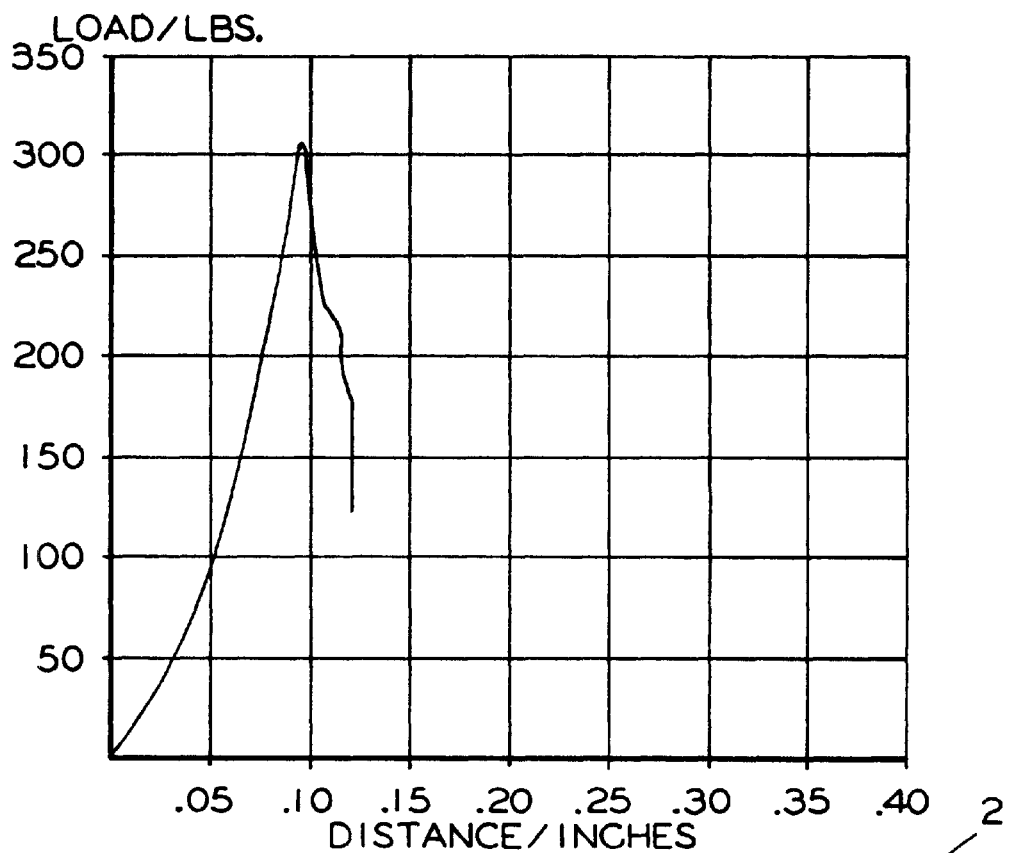
FIG. 3 is a graph showing a typical shear test.

In a typical test once the apparatus 10 is set up, a valve seal 14 is mounted in the mounting device 12 of lower fixture 6 and is supported or held in place by a retaining bolt 16. The apparatus then begins its test by moving the upper fixture 2, which supports the shearing means 18, in a downward direction at a rate of approximately 0.2 inches per minute. The upper fixture 2 with shearing means 18 meets the valve seal 14 and begins the force applied to the unit as directed by computer module 42. A graph records the Pounds of force and the distance in inches until the specimen break point has been reached. The chart is then printed and filed for reference. FIG. 3 illustrates a typical graph that is printed out from a specimen test. The graph in FIG. 3 is of test specimen which showed good adhesive bonding of the rubber and the brass insert. A control panel 44, shown in FIG. 4, permits an automatic control of the operation, however, the control could be performed manually.

In another embodiment of the instant invention there is provided a method for testing the shear strength of rubber bonded to a metal insert. The method comprises a first step of selecting a valve seal 14 to be tested.

Another step involves mounting such valve seal 14, selected in a previous step, in a lower fixture 6 of a test apparatus 10. Another step involves moving a shearing means 18 that is disposed in a radially opposed upper fixture 2 of the test apparatus 10 in a shearing direction (downward) by applying a force to the upper fixture 2. A next step is continuing the movement in the shearing direction of the upper fixture 2 of the test apparatus 10 until a bond between such rubber and such metallic insert is broken.

There is a step of measuring, in a predetermined unit of distance, the total movement of the upper fixture 2 of the test apparatus 10 and measuring, in a predetermined unit of force, the total force applied to the upper fixture 2 of such test apparatus 10 that was required to break such bond between such rubber and such metallic insert. Such method further includes a step of recording such total movement of the upper fixture 2 of such test apparatus 10, that was measured in a previous step, and such total force applied to the upper fixture 2 of said test apparatus 10, also measured in a previous step, on a graph.

The method further includes securing the valve seal 14 by means of a retainer bolt 16 in such mounting step described previously.

In the method such predetermined unit of distance, measured in a previous step is inches and such predetermined unit of force, also measured in a previous step, is pounds.

Such method further includes a step of displaying such total movement of the upper fixture 2 of the test apparatus 10 that was previously measured and such total force applied to the upper fixture 2 of the test apparatus 10 on a graph. Such displaying means includes a computer monitor 42.

While a presently preferred embodiment and alternate embodiments of the present invention has been described in detail above, it should be understood that various other adaptations and/or modifications of the invention can be made by those persons who are particularly skilled in the lighting art without departing from either the spirit of the invention or the scope of the appended claims.

I claim:

1. An apparatus for measuring a shear strength of rubber bonded to a metal insert in a valve seal, said apparatus comprising:
   (a) an upper fixture;
   (b) a radially opposed lower fixture, at least one of said upper fixture and said lower fixture being movable in a longitudinal direction with respect to one another;
   (c) a mounting device disposed in one of said lower fixture and said upper fixture for retaining such valve seal;
   (d) a shearing means disposed in an opposing one of said upper fixture and said lower fixture for shearing such rubber bonded to such metal insert in said valve seal, said shearing means having an arcuate edge for contacting said valve seal closely adjacent an interface between such rubber and such metal insert;
   (e) a first means engageable with said shearing means for controlling movement of said shearing means in one of a direction for shearing said valve seal and an opposite direction for returning said shearing means to its starting position; and
   (f) a second means in communication with said first means for recording such movement of said shearing means and for recording a force that is applied by said first means until a bond between such rubber and such metal insert of said valve seal is broken.

2. An apparatus, according to claim 1, wherein said apparatus further includes a third means in communication with said second means for displaying such distance said shearing means has moved and such force applied to said shearing means.

3. An apparatus, according to claim 1, wherein said second means records such movement of said shearing means and records such force that is applied by said first means in the form of a graph until a bond between such rubber and such metal insert of said valve seal is broken.

4. An apparatus, according to claim 1, wherein said arcuate edge is disposed on said shearing means so that a shear point is less than about 0.005 inches from an outer surface of such metal insert in said valve seal.

5. An apparatus, according to claim 4, wherein said arcuate edge of said shearing means is designed to shear said valve seal at such shear point where such bond is between such rubber and such metal insert.

6. An apparatus, according to claim 1, wherein said mounting device further includes a retainer bolt for securing said valve seal to one of said upper and said lower fixture.

7. An apparatus, according to claim 1, wherein said movement of said shearing means is measured in inches.

8. An apparatus, according to claim 1, wherein such force applied to said shearing means is measured in pounds.

9. An apparatus, according to claim 1, wherein said first means includes a computer module.

10. An apparatus, according to claim 1, wherein said first means includes a load cell.

11. An apparatus, according to claim 1, wherein said arcuate edge of said shearing means is not sharp.

12. An apparatus, according to claim 1, wherein said upper fixture is a movable fixture.

13. An apparatus, according to claim 1, wherein said shearing direction is downward.

14. A method for testing a shear strength of rubber bonded to a metallic insert, said method comprising:
   (a) selecting a valve seal to be tested;
   (b) mounting said valve seal, selected in step (a), in one of an upper and a lower fixture of a test apparatus;
   (c) moving a shearing means disposed in an opposite one of said upper fixture and said lower fixture of said test apparatus in a shearing direction by applying a force to said opposite one of said upper fixture and said lower fixture;
   (d) continuing said movement in said shearing direction of said opposite one of said upper fixture and said lower fixture of said test apparatus until a bond between such rubber and such metallic insert is broken;
   (e) measuring, in a predetermined unit of distance, said total movement of said opposite one of said upper fixture and said lower fixture of said test apparatus;
   (f) measuring, in a predetermined unit of force, a total force applied to said opposite one of said upper fixture and said lower fixture of said test apparatus required to break such bond between such rubber and such metallic insert; and
   (g) recording such total movement of said opposite one of said upper fixture and said lower fixture of said test apparatus measured in step (e) and such total force applied to said opposite one of said upper fixture and said lower fixture of said test apparatus measured in step (f).

15. A method, according to claim 14, wherein said mounting said valve seal in step (b) further includes securing said valve seal by means of a bolt.

16. A method, according to claim 14, wherein said predetermined unit of distance, measured in step (e), is inches.

17. A method, according to claim 14, wherein said predetermined unit of force, measured in step (f) is pounds.

18. A method, according to claim 14, wherein said method further includes a step of displaying such total movement of said opposite one of said upper fixture and said lower fixture of said test apparatus measured in step (e) and such total force applied to said opposite one of said upper fixture and said lower fixture of said test apparatus measured in step (f).

19. A method, according to claim 18, wherein said displaying means includes a computer monitor.

* * * * *